United States Patent [19]

Raspanti

[11] Patent Number: 5,518,713
[45] Date of Patent: May 21, 1996

[54] BENZOXAZOLE DERIVATIVES, THE USE THEREOF AS SUNSCREENS AND COSMETIC COMPOSITIONS CONTAINING THEM

[75] Inventor: Giuseppe Raspanti, Bergamo, Italy

[73] Assignee: 3V Inc., Weehawken, N.J.

[21] Appl. No.: 387,458

[22] Filed: Feb. 13, 1995

[51] Int. Cl.⁶ ............................................. A61K 7/42
[52] U.S. Cl. ............................ 424/59; 514/375; 548/217
[58] Field of Search ....................... 514/375; 548/221, 548/217; 424/59

[56] References Cited

U.S. PATENT DOCUMENTS

| | | | |
|---|---|---|---|
| 3,772,323 | 11/1973 | Schlapfer | 260/309.2 |
| 4,098,882 | 7/1978 | Lang | 424/59 |
| 5,362,481 | 11/1994 | Raspanti | 424/59 |

*Primary Examiner*—C. Warren Ivy
*Assistant Examiner*—Evelyn Huang
*Attorney, Agent, or Firm*—Griffin, Butler Whisenhunt & Kurtossy

[57] ABSTRACT

Benzoxazole derivatives having the following formula (I):

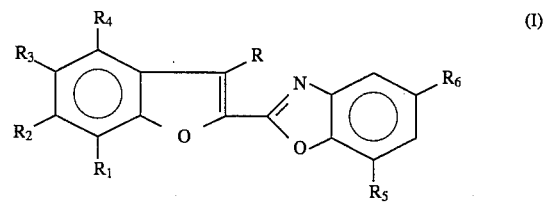

wherein the groups are hereinafter defined are disclosed together with the use thereof as sunscreen agents and cosmetic compositions containing them.

9 Claims, No Drawings

BENZOXAZOLE DERIVATIVES, THE USE THEREOF AS SUNSCREENS AND COSMETIC COMPOSITIONS CONTAINING THEM

The present invention relates to benzoxazole derivatives and the use thereof in cosmetic compositions.

BACKGROUND OF THE INVENTION

It is well-known that sunlight radiations ranging from 290 to 400 nm are noxious to the organic materials, among which human skin too, and particularly those radiations with wavelength between 290 and 320 nm, the so-called UV-B radiations, are responsible of the occurrence of erythema and sunburns, whose severity depend on exposition length.

It has been ascertained that also radiations comprised between 320 and 400 nm, so-called UV-A, which are responsible of skin tanning, can cause alterations and important damages in skin especially in the case of sensitive skin or in case of continuous exposure to the radiation. It has been shown that UV-A radiation, beside causing damages to elastin and collagen, the consequence of which is skin ageing, can also be the cause of a number of phototoxic and photoallergic reactions. Moreover, the noxious action of UV-B can also be enhanced by the presence of UV-A (Willis et al., Journal of Investigative Dermatology, vol. 59, 416, 1072).

In order to provide a protection against noxious UV-B radiation, a number of compounds are well-known and also used in cosmetic compositions, such as for example cinnamic acid, 4-aminobenzoic acid, benzylidenecamphor and benzophenone derivatives.

On the contrary, to date no sufficiently suitable products are available for the protection against UV-A, notwithstanding the patent literature provides many compounds as UV absorbers, but the practical result of them has not been satisfying.

A commercially available product is 2-hydroxy-4-methoxybenzophenone, whose maximum absorption at about 325 nm is too low to give an to effective protection, moreover its solubility in the solvents, usually used in cosmetics, is very low, thus making its use difficult. Another compound which is now used in practice is a dibenzoylmethane derivative, which however is insufficiently photostable ( Int. J. Cosm. Science 10, 53 1988 ) . Therefore, the sun protecting compositions containing these compounds can not guarantee a sufficient protection against UV-A, since the UV absorbers therein used are whether too weak (such as benzophenone derivative) or are too fast deteriorated by the radiation itself (such as dibenzoylmethane derivative).

Accordingly, nowadays cosmetic industry has not suitable products available for the effective protection of skin from sun radiations comprised between 320 and 400 nm.

DESCRIPTION OF THE INVENTION

It has now surprisingly been found that certain benzoxazole derivatives, other than a good photostability show a high absorption in the UV-A range. Therefore, they are particularly suitable for the use in cosmetic compositions for the skin protection against sun radiation.

The compounds according to the present invention are represented by the following formula (I):

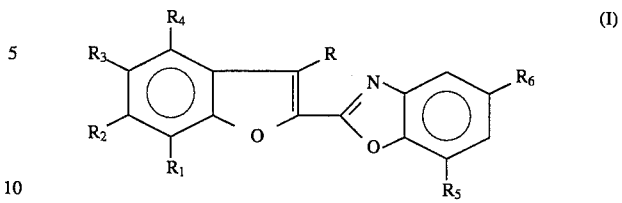

wherein R is hydrogen or the methyl or ethyl group,
$R_1$ is hydrogen or $C_1$–$C_8$ linear or branched alkyl,
$R_2$ is hydrogen or an —$OR_5$ group,
$R_3$ has the same meaning of $R_1$ or together with $R_4$ can form a carbocyclic ring,
$R_4$, other than the ring formed together $R_3$, is hydrogen,
$R_5$ is hydrogen or $C_1$–$C_4$ linear or branched alkyl,
$R_6$ has the same meaning of $R_5$ or is the —$COOR_7$ group, wherein $R_7$ is $C_1$–$C_{18}$ linear or branched alkyl or a glycol of formula (II):

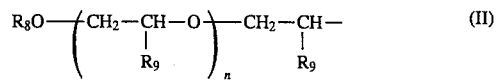

wherein $R_8$ is $C_1$–$C_4$ linear or branched alkyl, $R_9$ is hydrogen or methyl, n is a number from 0 to 4.

Some compounds of formula (I) are well-known. DE 2 238 628, DE 2 031 774, DE 2 361 338 and EP 0 010 063 disclose the preparation and use thereof as intermediate compounds for dyes, optical bleaching agents, or pharmaceutical products.

A possible use of these compounds as sunscreens in cosmetic compositions is neither disclosed nor suggested, The compounds according to the present invention absorb intensely UV radiations particularly in the range between 320 and 400 nm, further the compounds have a good photostability. Due to these UV-absorbing properties, the compounds can be used as sunscreens for the protection of organic material, such as synthetic polymers or especially in cosmetic compositions intended for the protection of skin against sun radiation noxious action.

According to the present invention, the following compounds are preferred for use in the preparation of cosmetic compositions:

1) 2-(2-benzofuranyl)-benzoxazole;
2) 2-(6-methoxy-2-benzofuranyl)-benzoxazole;
3) 2-(6-methoxy-2 -benzofuranyl)-5-methyl-benzoxazole;
4) 2-benzofuranyl) -5-methyl-benzoxazole;
5) 2-benzofuranyl)-5,7-dimethyl-benzoxazole;
6) 2-(2-benzofuranyl)-7-methyl-benzoxazole;
7) 2-(5-tert-butyl-2-benzofuranyl)-benzoxazole;
8) 2-(6-methoxy-2-benzofuranyl)-5-tert-butyl-benzoxazole;
9) 2-(3-methyl-2-benzofuranyl)-benzoxazole;
10) 2-(3-methyl-2-benzofuranyl)-5-tert-butyl-benzoxazole;
11) 2-(2-benzofuranyl)-5-carboethoxy-benzoxazole;
12) 2-(2-benzofuranyl)[5-carbo-(2-methoxyethoxy)]benzoxazole;
13) 2-(2-naphtho-[2.1-b]-furanyl)-benzoxazole;
14) 2-(2-naphtho-[2.1-b]-furanyl)-5-methyl-benzoxazole;
15) 2-(2-naphtho-[2.1-b]-furanyl)-5-tert-butyl-benzoxazole.

The above compounds are new except compounds 2, 3, 13 and 14.

Therefore, it is an object of the present invention a method of using the compounds of formula (I) above as sun screens.

Another object of the present invention are cosmetic compositions containing at least a compound of formula (I).

A further object of the present invention are compounds of formula (I):

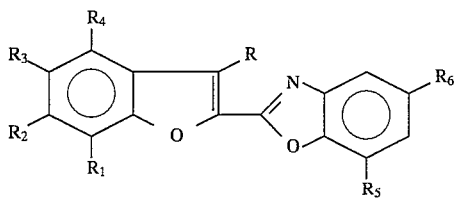

wherein R is hydrogen or methyl or ethyl group, $R_1$ is hydrogen or $C_1-C_8$ linear or branched alkyl, $R_2$ is hydrogen or a $-OR_5$ group, $R_3$ has the same meaning of $R_1$ or together with $R_4$ can form a carbocyclic ring, $R_4$, beside the ring together with $R_3$, is hydrogen, $R_5$ is hydrogen or $C_1-C_4$ linear or branched alkyl, $R_6$ has the same meaning of $R_5$ or is the $-COOR_7$ group, wherein $R_7$ is $C_1-C_{18}$ linear or branched alkyl or a glycol of formula (II):

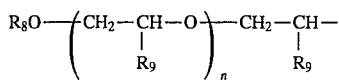

wherein $R_8$ is $C_1-C_4$ linear or branched alkyl, $R_9$ is hydrogen or methyl, n is a number from 0 to 4, the following compounds being excluded:

2-(6-methoxy-2-benzofuranyl)-benzoxazole;
2-(6-methoxy-2-benzofuranyl)-5-methyl-benzoxazole;
2-(2-naphtho-[2.1-b]-furanyl)-benzoxazole;
2-(2-naphtho-[2.1-b]-furanyl)-5-methyl-benzoxazole.

DETAILED DISCLOSURE OF THE INVENTION

The compounds according to the present invention are prepared according to well-known methods, for example according to the following scheme:

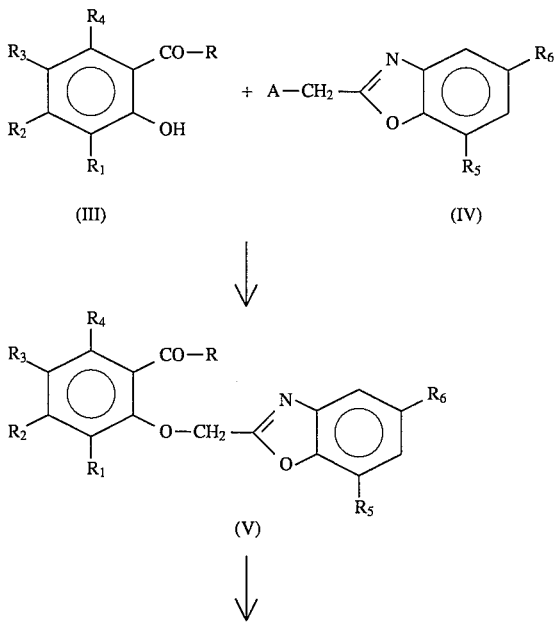

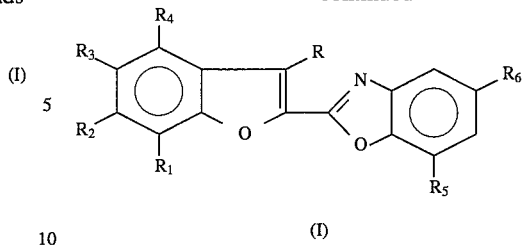

wherein $R-R_6$ have the above defined meanings, A is chlorine or bromine.

The reaction can be carried out in a polar solvent, such as for example alcohols, glycols, ethylene glycol monomethylether, diethylene glycol monomethyl ether, ethylene glycol monoethyl ether, propylene glycol, propylene glycol monomethyl ether, dimethyl formamide, N-methylpyrrolidone.

The reaction is carried out in the presence of bases, such as alkali or alkaline-earth metal hydroxides, alcoholates or carbonates at a temperature ranging from 20° to 200° C.

The intermediate compound (V) may be isolated, according to the process disclosed in DE 2 238 628 or, alternatively, the process may directly be carried out without isolating the benzyl ether (V), according to the method disclosed by Mathur and Mehra in J. Chem. Soc. C 1960, 1954.

The final compounds are purified according to conventional methods.

The intermediate compounds of formula (III) are well-known or can be prepared according to well-known methods, cloromethylbenzoxazoles (IV) are well-known too or can be prepared according to well-known processes from the corresponding 2-aminophenols and chloroacetyl chloride.

According to the present invention, the compounds of formula (I) are useful as sunscreens. Their skin protection activity against sun-radiations is exerted by applying a suitable amount on the skin zone exposed to radiations.

Therefore it is a further object of the present invention a method for the protection of skin from ultraviolet radiations of sunlight, comprising applying to the skin an ultraviolet radiation absorbing effective amount of a cosmetic composition having at least one compound of formula (I):

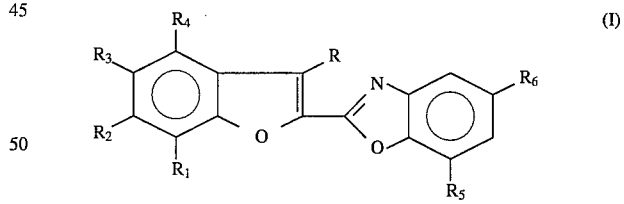

Suitable amounts for the applications can be determined by the man expert in the art depending on the specific extinction coefficient $E_1^1$ of the compounds of formula (I). Said coefficient is an index of the effectiveness of protection.

Beside the compounds of formula (I), according to the present invention, also other sun screens and particularly those absorbing at a wavelength from 290 to 320 nm, can be used in association.

In such a way a protection against both UV-A radiation and UV-B radiation is obtained. Well-known sunscreens that can be combined with compounds of formula (I) are for example:

3-(4-methylbenzylidene)-camphor, 2-ethylhexyl-(4-dimethyl-amino)benzoate, 2-ethylhexyl-(4-methoxy)-cinnamate, menthylsalicylate, 2-hydroxy-4-methoxy-benzophenone, 2,4,6-trianilino-(p-carbo-2-ethylhexyloxy)-1,3,5-triazine, triazine derivatives disclosed in EP 0 570 838, salts of 2-phenyl-benzimidazol-5-sulfonic acid or 2-hydroxy-4-methoxy-benzophenone-5-sulfonic acid. The application of the sunscreens of the present invention can be effected by means of cosmetic compositions containing one or more compounds of formula (I), optionally in combination with one or more well-known sunscreens, such as those above illustrated.

It is understood that the list of the sunscreens which can be combined with the compounds of formula (I) is not limited, but only illustrative.

The cosmetic compositions containing compounds of formula (I), object of the present invention, are useful for the treatment of skin, hairs or for the make-up, in decorative cosmetics. Said compositions may be of different kinds, for example solutions, lotions, water-in-oil or oil-in-water emulsions; or can be in the form of gels, lipstick, aerosols.

The cosmetic compositions of the present invention are prepared by formulating the usual carriers, such as for example oils, fats, emulgent agents, hydrating agents, moisturizing agents, emollient agents, preservatives, surfactants, thickening agents, antifoaming agents, perfumes, pigments, dyes and other else, such as alcohols, polyols, electrolites, silicone derivatives. The most commonly used solvents are triglycerides of caprinic or caprilic acid, for example castor oil, fatty acid esters, with isopropanol, or fatty alcohols esters with short chain carboxylic acid, alcohols, diols or polyols as well as the corresponding esters and particularly ethanol, isopropanol, propylene glycol, glycerine, ethylene glycol monoethyl ether, propylene glycol monomethyl-monoethyl or monobutyl ether.

The present invention also comprises the protection of the cosmetic compositions themselves against UV-A radiation by using the compounds of formula (I); in this case it is a matter of compositions whose components can undergo degradations or unwanted colours, due to sun light, such as for example shampoos and hair sprays, lotions and compositions for hair-set, compositions for hair dye, make-up formulations such as nail-lacquers, make-up base, lipsticks.

Cosmetic compositions for the skin protection against sun-radiations are preferred.

The cosmetic compositions, according to the present invention contain one or more compounds of formula (I) in amounts ranging from 0.1 to 20%, preferably from 0.5 to 15% by weight with respect to the total weight of the composition. The cosmetic compositions according to the invention, other than at least a compound of formula (I), may contain also in combination inorganic pigments, commonly used in cosmetics for the protection of the skin from UV radiations, such as for example titanium, zinc, silicon or aluminum oxides.

The following examples further illustrate the invention.

EXAMPLE 1

33.5 a of 2-chloromethyl-5-tert-butylbenzoxazole and 22 g of potassium carbonate were added to 19.5 g of salicylic aldehyde dissolved in 150 ml of ethylene glycol monomethyl ether. The reaction mixture was refluxed, while stirring for 2 hours, cooled down to room temperature then poured in 800 ml of water.

The precipitate which formed was filtered, washed with water and dried. Then it was crystallized from isopropanol in the presence of decolorizing earth.

2-(2-benzofuranyl)-5-tert-butyl-benzoxazole was obtained, in the form of a whitish substance with m.p. of 133°–135° C. and $E^1$ (MeOH) of 1482 at 328 nm and 1010 at 342 nm.

EXAMPLES 2–8

By operating as disclosed in Example 1, starting from the suitable salicylic aldehydes or 2-hydroxyacetophenones and from the corresponding 2-chloromethylbenzoxazoles, the compounds of formula (Ia) listed in Table 1 were prepared.

TABLE 1

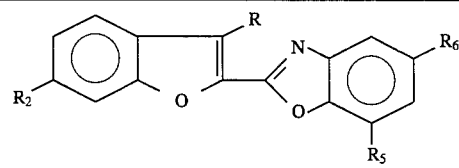

(Ia)

| Example | R | $R_2$ | $R_5$ | $R_6$ | m.p. °C. | $E_1^1$ | nm |
|---|---|---|---|---|---|---|---|
| 2 | H | H | H | H | 176–178 | 1765 / 1226 | 324 / 330 |
| 3 | H | H | H | $CH_3$ | 149–150 | 1653 / 1141 | 327 / 342 |
| 4 | H | H | H | $-COO-CH_2-CH_2-O-CH_3$ | 157–159 | 1405 / 1080 | 323 / 338 |
| 5 | $CH_3$ | H | H | $-C(CH_3)_3$ | 103–104 | 1474 / 986 | 328 / 344 |
| 6 | H | H | $CH_3$ | $CH_3$ | 132–133 | 1541 / 1028 | 327 / 343 |
| 7 | H | $CH_3O$ | H | H | 142–144 | 1572 / 1043 | 329 / 348 |
| 8 | H | $CH_3O$ | H | $CH_3$ | 124–126 | 1514 / 1005 | 328 / 348 |

EXAMPLES 9–11

By operating as disclosed Example 1, from 2-hydroxynaphthaldehyde and the corresponding 2-chloromethylbenzoxazoles, the compounds of formula (Ib) listed in Table 2 were obtained.

TABLE 2

(Ib)

[Structure of compound Ib with naphthalene-furan-benzoxazole system with R$_6$ substituent]

| Example | R$_6$ | m.p. °C. | E$_1^1$ | nm |
|---|---|---|---|---|
| 9 | H | 169–171 | 908 | 319 |
|   |   |   | 1612 | 348 |
|   |   |   | 1423 | 364 |
| 10 | CH$_3$ | 190–192 | 872 | 318 |
|   |   |   | 1541 | 348 |
|   |   |   | 1370 | 363 |
| 11 | —C(CH$_3$)$_3$ | 186–188 | 777 | 318 |
|   |   |   | 1353 | 347 |
|   |   |   | 1220 | 364 |

EXAMPLE 12

| Sun-milk | |
|---|---|
| Fatty acid triglyceride | 20.0 g |
| Cetyl alcohol | 2.0 g |
| Cetylstearyl alcohol | 2.0 g |
| Lanolin | 4.0 g |
| Silicone oil | 0.4 g |
| 2-ethylhexyl-4-dimethylaminobenzoate | 2.5 g |
| Compound of Example 6 | 2 g |
| Abiol$^{(R)}$ (preservative by 3V-SIGMA) | 0.2 g |
| Syntalen M$^{(R)}$ (crosslinked polyacrilic acid by 3V SIGMA) | 0.1 g |
| Triethanolamine | 0.15 g |
| Perfume | 0.3 g |
| Distiled water q.s. | 100 g |

The fatty phase was warmed at 80°–90° C., the sunscreen of Example 6 was added, then the mixture was added into water, containing the hydrosoluble compounds, warmed at 80°–90° C. Stirring under heating was continued still for 15–20 minutes. The mixture was slowly cooled then perfume was added.

EXAMPLE 13

| Day cream | |
|---|---|
| (C$_8$–C$_{18}$) acid triglyceride | 29.0 g |
| Glycerine monostearate | 7.0 g |
| Stearic acid | 2.0 g |
| Lanolin | 4.0 g |
| Preservative | 0.2 g |
| Compound of Example 4 | 2.5 g |
| Propylene glycol | 2.5 g |
| Triethanolamine | 0.5 g |
| Perfume | 0.3 g |
| Distiled water q.s. | 100 g |

The preparation was carried out as disclosed in Example 12.

EXAMPLE 14

| Sun cream | |
|---|---|
| Benzoate of C$_{12}$–C$_{15}$ alcohols (Finisol TN$^{(R)}$, Witco) | 5.0 g |
| Cetylstearyl alcohol | 3.0 g |
| Glycerine mono and distearate | 4.0 g |
| Polyglycol (Arlacel 165$^{(R)}$ C, ICI | 2.0 g |
| Myristic alcohol with 3 mole of propyleneoxide (Witconol$^{(R)}$ APM-Witco) | 21.0 g |
| Compound of Example 5 | 2.5 g |
| 2-Ethylhexyl-4-methoxycinnamate | 3.5 g |
| Perfume | 0.3 g |
| Distiled water q.s. | 100 g |

The composition was carried out as in Example 12.

EXAMPLE 15

| Lipstick | |
|---|---|
| Firstly it was prepared the base mixture consisting of: | |
| Beeswax | 13.0 g |
| Carnauba wax | 7.5 g |
| Lanolin | 5.0 g |
| Isopropyl myristate | 8.0 g |
| Mineral oil | 3.0 g |
| Castor oil | 63.5 g |

85 g of the above mixture were warmed till fusion, 7 g of compound of Example 1 and 8 g of 3-(4-methylbenzylidene)camphor, as well as perfume, aroma and dyes were added to the melted mass, then it was diluted to 1000 g with castor oil and cooled down to room temperature.

EXAMPLE 16

| Alcoholic gel | |
|---|---|
| Propylene glycol | 25.0 g |
| Ethyl alcohol 96% | 25.0 g |
| Synthalen M$^{(R)}$ (crosslinked polyacrylic acid by 3V SIGMA) | 0.6 g |
| Compound of Example 11 | 2.0 g |
| Trietbanolamine | 0.3 g |
| Preservative | 0.3 g |
| Perfume | 0.3 g |
| Distiled water q.s. | 100 g |

Synthalen M was dispersed in water, then triethanolamine and the mixture of propylene glycol and ethanol, wherein the compound of Example 11 had been previously dissolved, were added.

I claim:

1. A cosmetic composition comprising a cosmetic acceptable carrier and a UV-A ultraviolet radiation absorbing amount of from 0.5 to about 20% by weight with respect to the total weight of the composition of at least one compound of formula (I):

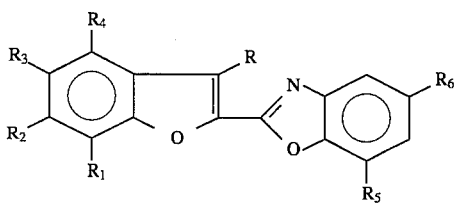

wherein R is hydrogen or the methyl or ethyl group,

R₁ is hydrogen or C₁–C₈ linear or branched alkyl,

R₂ is hydrogen or a —OR₅ group,

R₃ has the same meaning of R₁ or together with R₄ can form a carbocyclic ring,

R₄, beside the ring together with R₃, can be hydrogen,

R₅ is hydrogen or C₁–C₄ linear or branched alkyl,

R₆ has the same meaning of R₅ or is the —COOR₇ group, wherein R₇ is C₁–C₁₈ linear or branched alkyl or a glycol of formula (II):

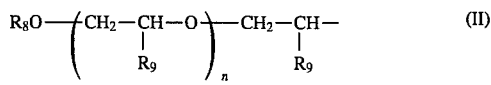

wherein R₈ is C₁–C₄ linear or branched alkyl, R₉ is hydrogen or methyl, and n is a number from 0 to 4.

2. A composition according to claim 1, containing up to 0.5 to 15% by weight of at least one compound of formula (I).

3. A composition according to claim 1 containing at least one of the following compounds:

2-(2-benzofuranyl)-benzoxazole;
2-(6-methoxy-2-benzofuranyl)-benzoxazole;
2-(6-methoxy-2-benzofuranyl)-5-methyl-benzoxazole;
2-(2-benzofuranyl )-5-methyl-benzoxazole;
2-(2-benzofuranyl)-5,7-dimethyl-benzoxazole;
2-(2-benzofuranyl)-7-methyl-benzoxazole;
2-(5-tert-butyl-2-benzofuranyl)-benzoxazole;
2-(6-methoxy-2-benzofuranyl)-5-tert-butyl-benzoxazole;
2-(3 -methyl-2-benzofuranyl)-benzoxazole;
2-(3-methyl-2-benzofuranyl)-5-tert-butyl-benzoxazole;
2-(2-benzofuranyl)-5 -carboethoxy-benzoxazole;
2-(2-benzofuranyl)-[5-carbo(2-methoxyethoxy)]benzoxazole;
2-(2-naphtho-[2.1-b]-furanyl)-benzoxazole;
2-(2-naphtho-[2.1-b]-furanyl)-5-methyl-benzoxazole;
2-(2-naphtho-[2.1-b]-furanyl )-5-tert-butyl-benzoxazole.

4. Cosmetic compositions according to claim 1, also containing one or more of UV-A sunscreens UV-B sunscreens and inorganic pigments.

5. Cosmetic compositions according to claim 4, wherein the UV-B sunscreens are selected form the group consisting of 3-benzylidenecamphor derivatives, 4-aminobenzoic acid derivatives, esters of 4-methoxycinnamic acid derivatives, salicylic acid derivatives, benzophenone derivatives, 2,4,6-trianilino-(p-carboethylhexyloxy)- 1,3,5-triazine, 2-phenyl-benzimidazole- 5-sulfonic acid salts, 2-hydroxy- 4-methoxy-benzophenone-5-sulfonic acid salts and acid 3-benzylidenecamphorsulfonic salts.

6. A method for the protection of skin from ultraviolet sunlight radiations, comprising applying to the skin an ultraviolet radiation absorbing effective amount of a cosmetic composition according to claim 1.

7. A method for the protection of a cosmetic composition from degradations or unwanted colours, due to sunlight UV-A radiation comprising including a compound of formula (I)

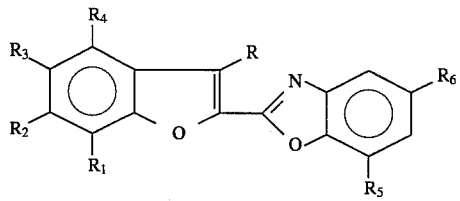

wherein R is hydrogen or the methyl or ethyl group,

R₁ is hydrogen or C₁–C₈ linear or branched alkyl,

R₂ is hydrogen or a —OR₅ group,

R₃ has the same meaning of R₁ or together with R₄ can form a carbocyclic ring,

R₄, beside the ring together R₃, can be hydrogen,

R₅ is hydrogen or C₁–C₄ linear or branched alkyl,

R₆ has the same meaning of R₅ or is the —COOR₇ group, wherein R₇ is C₁–C₁₈ linear or branched alkyl or a glycol of formula (II):

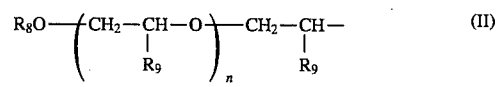

wherein R₈ is C₁–C₄ linear or branched alkyl, R₉ is hydrogen or methyl, n is a number from 0 to 4.

8. A compound of formula (I):

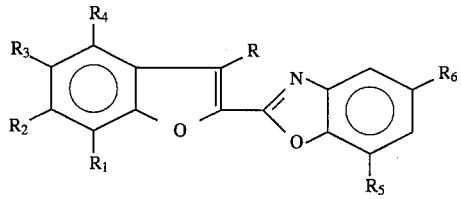

wherein R is hydrogen or the methyl or ethyl group,

R₁ is hydrogen or C₁–C₈ linear or branched alkyl,

R₂ is hydrogen or a —OR₅ group,

R₃ has the same meaning of R₁ or together with R₄ can form a carbocyclic ring,

R₄, beside the ring together with R₃, can be hydrogen,

R₅ is hydrogen or C₁–C₄ linear or branched alkyl,

R₆ has the same meaning of R₅ or is the —COOR₇ group, wherein R₇ is C₁–C₁₈ linear or branched alkyl or a glycol of formula (II):

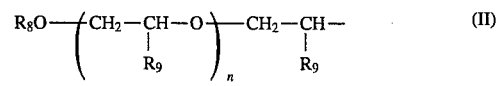

wherein R₈ is C₁–C₄ linear or branched alkyl, R₉ is hydrogen or methyl, n is a number from 0 to 4, provided that when R₅ is hydrogen R₆ is not hydrogen and not C₁–C₄ linear or branched alkyl, and with the exclusion of the following compounds:

2-(6-methoxy-2-benzofuranyl)-benzoxazole;
2-(6-methoxy-2-benzofuranyl)-5-methyl-benzoxazole;
2-(2-naphtho-[2.1-b]-furanyl)-benzoxazole; and
2-(2-naphtho-[2.1-b]-furanyl)-5-methyl-benzoxazole.

9. A compound according to claim 8, wherein the compound is 2-(2-benzofuranyl)-5,7-dimethylbenzoxazole.

\* \* \* \* \*